United States Patent [19]

Kratochvil et al.

[11] 4,449,011
[45] May 15, 1984

[54] METHOD AND APPARATUS FOR ENCAPSULATION OF CHEMICALLY SENSITIVE FIELD EFFECT DEVICE

[75] Inventors: Jiri Kratochvil, Sandy; Nelson Ho, West Valley; Jiri Janata, Salt Lake City, all of Utah

[73] Assignee: Critikon, Inc., Tampa, Fla.

[21] Appl. No.: 350,929

[22] Filed: Jan. 8, 1982

[51] Int. Cl.³ ............................................. H05K 5/00
[52] U.S. Cl. .............................. 174/52 PE; 339/17 F
[58] Field of Search .......... 174/52 PE, 52 FP, 117 F, 174/117 FF; 339/17 F, 17 M

[56] References Cited

U.S. PATENT DOCUMENTS 3,393,392  7/1968  Shelley ............................ 339/17 F
4,020,830  5/1977  Johnson et al. ................. 357/26 X
4,132,856  1/1979  Hutchison et al. ............ 174/52 PE
4,135,038  1/1979  Takami et al. ................. 174/52 FP Primary Examiner—J. V. Truhe
Assistant Examiner—D. A. Tone
Attorney, Agent, or Firm—Audley A. Ciamporcero, Jr.

[57] ABSTRACT

Semiconductor chips carrying chemically sensitive field effect devices are encapsulated by tape automated bonding techniques, wherein one tape layer has a beam lead pattern disposed thereon which terminates in the chip bonding pad pattern over an opening in the tape. A tape layer for sealably covering the beam lead pattern and the chip has openings which are respectively coincident with the chemically selective membrane systems of the field effect devices.

4 Claims, 2 Drawing Figures

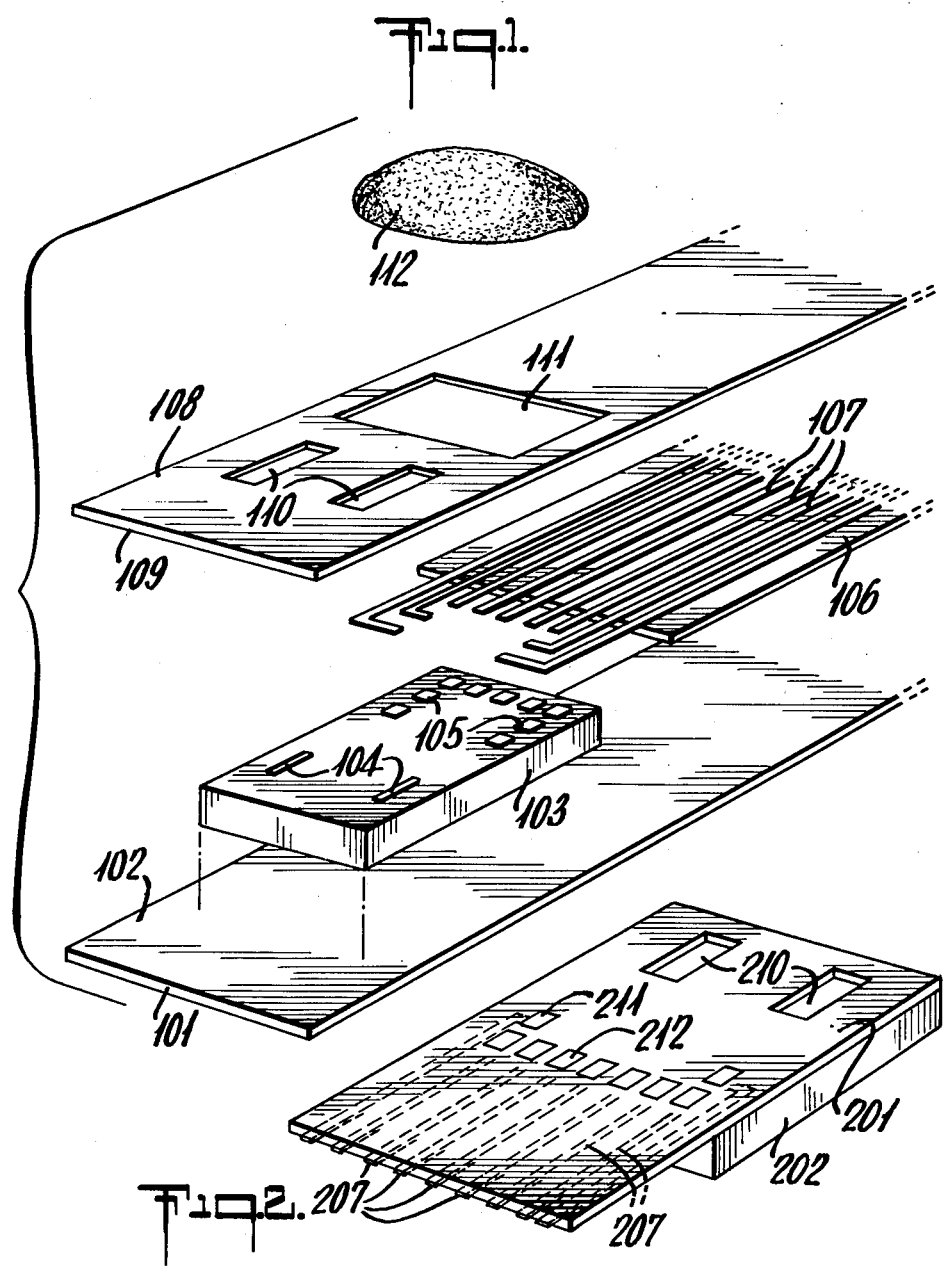

METHOD AND APPARATUS FOR ENCAPSULATION OF CHEMICALLY SENSITIVE FIELD EFFECT DEVICE

FIELD OF THE INVENTION

This invention relates to semiconductor devices whose electrical characteristics are dependent on the selective interaction of a portion thereof with specified substances, and more particularly to methods and apparatus for encapsulation of such devices for use in disparate ambient environments.

BACKGROUND OF THE INVENTION

There exists a class of devices exemplified by U.S. Pat. No. 4,020,830 to Johnson et al., dated May 3, 1977, entitled SELECTIVE CHEMICAL SENSITIVE FET TRANSDUCERS. These devices feature electrical conduction characteristics which are modulated by the interaction of a chemically selective system with ambient materials. In accordance with the Johnson patent, a substrate layer carries respective drain and source regions, separated by a region or channel over which is disposd an insulating layer and a chemically selective system for specified interaction with predetermined ambient materials. The chemically selective system generally takes the form of a membrane which interacts with materials, and modulates the drain to source electrical current based on concentrations of the specified ambient substances.

The Johnson et al. patent contemplates chemically selective systems for measuring various types of ambient conditions, including gas concentrations, ion activity, immunochemical concentrations, concentrations of enzymes, and the like, and indeed many such applications have engendered widespread interest in a variety of disparate fields. While the nomenclature in the art has tended to designate these respective applications separately, for example using the designation "CHEMFET" for chemically selective membrane devices, "ISFET" for ionically reactive devices, 37 IMMUNOFET" for immunologically reactive devices, and so forth, for purposes of this application the term "chemfet", or simply "device" shall be utilized generically to encompass all such apparatus, irrespective of the type of sensing or reaction utilized, the character of the membrane employed, or the nature of the ambient substance to be monitored. Likewise, the term "chemfet" or "device" as used herein shall embrace transistor type, diode type, or the like other devices which feature similar conductivity modulation based on membrane-substance interactions.

In recent times, much effort has been expended in the development of device configurations in manufacturing processes which will facilitate large-scale production of reliable, stable, and well-calibrated devices. For example, device encapsulation, membrane formulation, and membrane disposition have proven to be formidable technical problems.

It is a general object of the principles of the present invention to provide encapsulation apparatus and compatible assembly processes for the production of chemfet devices which have high reliability, well quantified specifications, improved physical integrity, and a reasonable operational lifespan.

The packaging or encapsulation problems attendant to chemfet devices are highly demanding and somewhat unique in the semiconductor fabrication field. The devices themselves are quite small, and rely in their operation on the exposure of even smaller chemically sensitive gate portions with ambient solution environments. With the exception of the miniature gate portions, however, the remainder of the semiconductor chip and associated connections, including conductive lines, chip edges, and bonding pad connections, must be hermetically sealed. Failure so to seal these portions of the device engenders corrosion problems and eventual device degradation and failure, and, in the worse case, extraneous electrical paths between conductors in the device system. Furthermore, with particular reference to biomedical applications, exposure of any portion of the system, other than the chemically sensitive gate region, raises the risk of untoward contamination of the biological materials being monitored.

It is accordingly an object of the present invention to provide encapsulation systems and techniques which are compatible with the dimensions and fragility of the devices and especially their chemically sensitive membrane systems.

A popular, although tedious technique for chemfet device encapsulation involves utilization of a hollow, catheter style flexible tube. Small gauge wires are threaded through the catheter, and at one end are soldered to any of a variety of commercially available connectors for plug in to monitoring circuitry. At the other end, the wires are epoxied and cut, leaving bare strands for connection of the chip. Next, the semiconductor chip carrying one or more devices is epoxied to the catheter and small (e.g., 0.001 inch diameter) wires are ultrasonically bonded between the chip bonding pads and the exposd wire end strands from the catheter. Once correct electrical contact has been verified, a thixotropic epoxy is applied by hand to cover all of the chip and wires, but leaving exposed small open areas around the chemically sensitive gate membrane portion of the devices.

The foregoing procedure has for the most part been moderately successful in the production of working devices, but clearly involves considerable time, training, and skill on the part of the assembler. Additionally, the essentially "hand-made" nature of each device yields a nonuniform product; this nonuniformity often leads to variation in performance as various membranes are applied to the units. Furthermore, the ultrasonic wire bonding step necessarily produces a nonplanar loop, which also must be encapsulated, but the encapsulation of which engenders further structural risk to the device during the encapsulation process. Finally, the nonplanar nature of this encapsulation further contributes to the functional nonuniformity of the devices so produced.

It is an important object of the principles of the present invention to obviate the difficulties, drawbacks, and uncertainties essentially attendant to the foregoing "hand-made" chemfet encapsulation techniques, as well as the functional uncertainties and nonuniformities necessarily resulting therefrom.

A technique which has recently found favor in the semiconductor industry for the enclosure of semiconductor chips is the so-called tape automated bonding process. See, for example, an article in *Solid State Technology*, March 1978, by Cain entitled "Beam Tape Carriers--A Design Guide", or an article in *EDN*, Aug. 20, 1977 by Palstone entitled "Beam--Tape Technology". Generally, conventional tape automated bonding techniques employ the use of a flat copper lead pattern, often defined on a substrate by photolithographic process, to which the semiconductor chip is bonded. Thereupon, either the chip and beam leads are separated and used, or the entire assembly is suitably fully enclosed.

It is an object of the present invention to adapt tape automated bonding techniques to the encapsulation of chemfet-style devices.

SUMMARY OF THE INVENTION

In accordance with the principles of the present invention, tape automated bonding techniques, a relatively recent development in the semiconductor industry, are adapted to the unique encapsulation criteria associated with CHEMFET-style devices. In accordance with the principles of the present invention, a flat, substantially nonreactive tape or film supports a flat copper lead pattern. In preferred embodiments, the tape is a polyimide material which is known to be nonreactive under a wide variety of circumstances, and especially to be biocompatible. The polyimide tape defines an opening or terminus for receipt of the devices, but the beam lead pattern extends over the opening, and terminates in a pattern essentially congruent with the bonding pad pattern of the device. The semiconductor chip carrying the CHEMFET device is bonded to the beam lead ends, for example by ultrasonic bonding.

Other films or tapes, preferably also polyimide, cover the chip on both its top and its bottom, but define windows overlying at least the gate membrane area of the CHEMFET devices. Thermosetting silicone adhesives provide for adequate exposure of the membrane areas of the CHEMFETS, but forms an adequate seal and protection for the rest of the device. Backing layers and/or overlayment for the bonding pads may alternatively be provided either by further tape layers or by potting processes.

It will be appreciated, then, in accordance with the principles of the present invention, that the tape automated bonding process is utilized successfully in a device which is partially exposed and partially enclosed, but with hermetic seals of the boundaries therebetween. The flat copper lead pattern, in conjuction with the CHEMFET bonding pad configuration, is compatible with bonding processes appropriate for the CHEMFET devices, and provides electrical conduction characteristics which are operational in the signal and voltage ranges, and ambient environmental conditions normally experienced by CHEMFETs, for example in biomedical monitoring functions. More importantly, the encapsulation apparatus and method of the present invention permits production of uniform devices, of determinable, relatively uniform and well characterized quality and performance specifications.

DESCRIPTION OF THE DRAWINGS

FIG. 1 shows in exploded form a preferred embodiment of the principles of the present invention.

FIG. 2 shows an alternative embodiment of the principles of the present invention.

BEST MODE FOR CARRYING OUT THE INVENTION

With reference to FIG. 1, the following describes preferred methods for fabricating prefered apparatus in accordance with the principles of the present invention. In FIG. 1, a semiconductor chip 103 is shown having a "U" shaped series of electrical bonding pads 105, and oppositely disposed therefrom a pair of gate membrane electrodes 104. It will be understood that the chip 103 shown in the drawing thereby carries two separate CHEMFET devices, each gate membrane 104 constituting the selectively responsive portion thereof, and each device being connected to exterior circuitry through a suitable number of the bonding pads 105. In particular, the bonding pads, as is known in the art, provide connection to the drain and source electrodes, substrate and reference electrodes, and associated biasing and temperature compensation circuitry. The general device configurations, electrical operational characteristics, and the like will be readily appreciated upon consideration of the aforementioned Johnson et al. patent. It will likewise be appreciated that the patterns of the bonding pads 105 on any given chip will vary, but in any event such bonding pad location and pattern configuration will be known to a high degree of precision, hence rendering the principles of the present invention readily applicable to virtually any such configuration. Likewise, the location, size, and physical nature of the gate membrane electrically 104 will constitute a critical and hence extremely well-characterized aspect of the device, and correspondingly will be well quantified for application of the principles of the present invention.

In FIG. 1, a substrate layer 101 forms a support mechanism for assembly and, in preferred embodiments, a backing and protection layer for the chip 103 and its associated physical and electrical interconnections. In such preferred embodiment, the tape backing layer 101 is a polyimide film such as the one commercially available from Du Pont under the trade designation, "Kapton", which is coated on its upper side with a suitable adhesive 102.

In accordance with a preferred form of the principles of the present invention, another film or tape layer 106 carries a series of beam leads 107, which in accordance with known tape automated bonding procedures are formed of copper or copper based materials defined on the tape 106 by a photolithographic process. In accordance with the principles of the present invention, the leads 107 extend beyond the edge of the tape 106, respectively terminating relative to one another in positions which are substantially congruent with the configuration of the bonding pads 105 of the device 103. In fact, as will be noted from the drawing, the terminal points of the leads 107 are situated for precise overlayment, and electrical interconnection with the various bonding pads 105 of the CHEMFET devices. In a preferred embodiment of the principles of the present invention, the tape 106 also is polyimide film or tape, for example, that of the Du Pont "Kapton" brand. In the drawing, the beam leads 107 are shown extending beyond a terminus of the tape 106, but it will also be appreciated that in alternative formulations, the area shown in the drawing as occupied by the chip 103 may merely be a recess or opening in a continuous length of tape 106, with the beam lead 107 extending out over that opening.

FIG. 1 also shows an upper tape layer 108, the lower side of which 109 is coated with a thermosetting silicone adhesive. The upper tape is, advantageously, polyimide film or the like biocompatible and substantially nonreactive film products currently available. The tape 108 defines a pair of windows 110 for location over and about the gate membrane areas 104, and exposure of those areas to the ambient environment as the encapsulated device is put into use. Optionally, another opening 111 is provided for exposure of the bonding pads 105 and the extending terminations of the beam lead 107. An epoxy or the like encapsulant is later to be provided for the bonding pad window 111, once the bonding processes are completed.

In a preferred method of encapsulating devices, once the configuration of the respective relevant areas of the chip 103 are determined, suitable copper lead patterns are provided for the leads 107, and the windows 110 and 111 are provided in the upper tape layer, for example by chemical etching, laser cutting, or mechanical cutting or punching. The device 103 is applied to the substrate 101, and the middle tape 106 is provided with the beams 107 having their respective terminations in precise, predetermined registry with their associated bonding pads on the chip 105. Thereupon, the leads are bonded to the pads. In one method of bonding, each of the leads is individually bonded utilizing ultrasonic bonding procedures. In another, prior to application of the tape 106 as shown, "bumps" of connector material are plated onto the bonding pads (i.e., during the device fabrication process), and as the leads 107 are placed in registry with the bonding pads 105, a heating tool shaped and located in congruency therewith supplies heat and compression so that all leads 107 are simultaneously bonded to the pads 105 through the heating, melting, and subsequent cooling of the plated "bumps" on the device.

In either event, after the coupling of the leads to the device, the top tape 108 is placed over the device 103 and the intermediate tape or film 106, with the emphasis being on the precise alignment of the membrane windows 110 with the respective gate membrane areas 104. In fact, the bonding pad window 111 is provided in preferred embodiments to facilitate alignment and/or realignment of the top tape 108 relative to the device 103 without causing stress to the beam lead bonds at pads 105. Clearly, however, any application and alignment procedure which is sufficiently precise as to obviate the need for such realignment, will likewise obviate the need for the bonding pad window 111. Once precise alignment is achieved, the thermosetting silicone adhesive 109, which is affixed over the device except at the open windows 110, is subjected to its thermosetting curing conditions, whereupon the chip 103 will be completely sealed from ambient conditions with the exception of the gate membrane area 104, and the bonding pad window 111. The bonding pads are completely and hermetically sealed by application of the potting encapsulant 112, for example epoxy.

The device thereby is completely encapsulated, and is ready for application of membrane materials in the windows 110 and over the gate membrane areas 104, and utilization, for example by immersion into biological solutions or environments.

It will be appreciated that the lower tape 101, while providing a suitable support and compatible seal for the device, may be replaced by a nonadhesive working surface which does not become a part of the device. In such event, after application and setting of the top tape 108, the back and sides of the device 103 may be enclosed by appropriate material, for example, epoxy, liquid polyimide, or machined or molded support mechanisms.

FIG. 2 shows an alternative embodiment of the principles of the present invention. In FIG. 2, a single tape layer 201 takes the place of tape layers 106 and 108 of FIG. 1. Hence, in FIG. 2, the beam leads 207 are plated on the underside of the tape 201, and the chip 202 (as in FIG. 1, an exemplary chip carrying two devices) is adhered to the underside of the tape 201. Openings are cut in the tape 201 both for the beam lead terminations (i.e., openings 211, 212, etc.) in congruence with the chip bonding pads, and for the gate membrane areas (i.e., openings 210) in congruence with the CHEMFET gate membrane systems. As in the case of the FIG. 1 embodiment, the beam leads opening 211, 212, etc., are filled, as by potting, after the leads are attached to the bonding pads. Further, the lower sides of the tape 201, and the chip 202, are sealed thereafter either by a separate tape (identical to tape 101 in FIG. 1), or by other suitable inert, compatible seals, such as potting.

It will similarly be understood that those of ordinary skill in the art will fashion numerous embodiments and alternative configurations which will be included within the spirit and scope of the present invention.

We claim:

1. For use in an apparatus employing a semiconductor chip having lead bonding pads and carrying at least one chemically sensitive field effect device which interacts with select ambient substances by means of one or more exposed selectively reactive membrane systems, an encapsulation system comprising:

tape means having conductive beam leads disposed thereon, said tape means defining an area to accommodate said chip, said beam leads terminating in first ends over said area, said tape means further defining first openings which are respectively adapted to be coincident with said membrane systems; wherein said tape means comprises respective first and second tapes, said first tape carrying said beam leads and said second tape defining a second opening coincident with the first ends of said beam leads, said first tape further defining said first openings; said tape means sealably overlaying at least said beam leads; whereby said tape means and a chip when connected thereto, will be aligned to leave exposed only at least a portion of each of said membrane systems.

2. An encapsulation system as described in claim 1 wherein said means to sealably overlay comprises a third tape.

3. An encapsulation system as described in claim 1 wherein said first and second tapes are respectively oppositely facing members and are substantially nonreactive to said ambient substances.

4. For use in an apparatus employing a semiconductor chip having lead bonding pads and carrying at least one chemically sensitive field effect device which interacts with select ambient substances by means of one or more exposed selectively reactive membrane systems, an encapsulation system comprising:

tape means having conductive beam leads disposed thereon, said tape means defining an area to accommodate said chip, said beam leads terminating in first ends over said area, said tape means further defining first openings which are respectively adapted to be coincident with said membrane systems; wherein said tape means defines second openings coincident with the first ends of said beam leads for affixation of said beam leads and carries said beam leads on a lower side for facing said chip, said tape means defining an outer hermetic seal for said device except for said openings; and wherein said system further comprises sealing means for oppositely facing said lower side, said beam leads and a back side of said device; said tape means sealably overlaying at least said beam leads; whereby said tape means and a chip when connected thereto, will be aligned to leave exposed only at least a portion of each of said membrane systems.

* * * * *